US008323339B2

(12) United States Patent
Fischer

(10) Patent No.: US 8,323,339 B2
(45) Date of Patent: *Dec. 4, 2012

(54) METHODS OF MANUFACTURING A DELIVERY SYSTEM FOR PROMOTING BONE GROWTH

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 351 days.

This patent is subject to a terminal disclaimer.

(21) Appl. No.: 12/202,886

(22) Filed: Sep. 2, 2008

(65) Prior Publication Data

US 2008/0317817 A1    Dec. 25, 2008

Related U.S. Application Data

(62) Division of application No. 10/766,503, filed on Jan. 28, 2004, now Pat. No. 7,534,264.

(51) Int. Cl.
*A61F 2/28* (2006.01)
(52) U.S. Cl. ...................... 623/16.11; 424/549
(58) Field of Classification Search ........................ None
See application file for complete search history.

(56) References Cited

U.S. PATENT DOCUMENTS

| | | | |
|---|---|---|---|
| 2,423,707 A | 7/1947 | Kenyon et al. |
| 4,439,420 A | 3/1984 | Mattei et al. |
| 4,440,750 A | 4/1984 | Glowacki et al. |
| 4,578,055 A | 3/1986 | Fischer |
| 4,728,570 A | 3/1988 | Ashman et al. |
| 4,755,184 A | 7/1988 | Silverberg |
| 4,863,472 A | 9/1989 | Tormala et al. |
| 5,098,299 A | 3/1992 | Fischer |
| 5,292,253 A | 3/1994 | Levy |
| 5,534,562 A | 7/1996 | Jensen et al. |
| 5,620,702 A | 4/1997 | Podell et al. |
| 5,635,162 A | 6/1997 | Fischer |
| 5,707,962 A | 1/1998 | Chen et al. |
| 5,787,901 A | 8/1998 | Wilson |
| 5,837,258 A | 11/1998 | Grotendorst |
| 5,910,315 A | 6/1999 | Stevenson et al. |
| 5,958,441 A | 9/1999 | Oppermann et al. |
| 5,985,315 A | 11/1999 | Patat et al. |
| 6,180,606 B1 | 1/2001 | Chen et al. |
| 6,287,341 B1 | 9/2001 | Lee et al. |
| 6,297,213 B1 | 10/2001 | Oppermann et al. |
| 6,306,424 B1 | 10/2001 | Vyakarnam et al. |
| 6,326,018 B1 | 12/2001 | Gertzman et al. |
| 6,372,257 B1 | 4/2002 | Marchosky |
| 6,440,427 B1 | 8/2002 | Wadstrom |
| 6,458,162 B1 | 10/2002 | Koblish et al. |
| 6,565,606 B1 | 5/2003 | Bruce et al. |
| 6,565,884 B2 | 5/2003 | Nimni |
| 6,576,249 B1 | 6/2003 | Gendler et al. |
| 6,599,517 B1 | 7/2003 | Ljusberg-Wahren et al. |
| 6,652,840 B1 | 11/2003 | Prevendar |
| 2003/0009147 A1 | 1/2003 | Bonutti |
| 2003/0026770 A1 | 2/2003 | Szymaitis |
| 2003/0135214 A1 | 7/2003 | Fetto et al. |
| 2003/0147860 A1 | 8/2003 | Marchosky |
| 2003/0166274 A1 | 9/2003 | Hewitt et al. |
| 2003/0194380 A1 | 10/2003 | Szymaitis |
| 2007/0071791 A1 | 3/2007 | Fischer |

FOREIGN PATENT DOCUMENTS

| | | |
|---|---|---|
| DE | 69403439 | 10/1997 |
| DE | 69429801 | 7/2002 |
| DE | 69819329 | 5/2004 |
| EP | WO9639203 | 12/1996 |

OTHER PUBLICATIONS

Cook, S.D., "Enhanced Bone Ingrowth and Fixation Strength With Hydroxyappatite-Coated Porous Implants" Database: PMID, Accession No. 10171176, Semin Arthroplasty. Oct. 1991.
Damien, CJ, "Effect of Demineralized Bone Matrix on Bone Growth Within a Porous HA Material: A Histologic and Histometric Study" Database: PMID Accession No. 9309501, J. Biometer Appl. Jan. 1995.
Cook, S.D., "The Effect of Demineralized Bone Matrix on Gel on Bone Ingrowth and Fixation of Porous Implants" J. Database: PMID, Accession No. 12066267 Arthroplasty, Jun. 2002.
Chiroff, R.T., "Tissue Ingrowth of Replamineform Implants" J. Biomed Mater Res. Jul. 1975. http://www.sodbrennedn-welt.de/science/1975.
University of Oxford, Project No. 542 "Bone Bonding Spheres" htt://www.isis-innovation.com/licensing/542.html—At least as early as Sep. 16, 2003.
Office Action dated May 25, 2007 cited in U.S. Appl. No. 10/766,503.
Office Action dated Sep. 11, 2007 cited in U.S. Appl. No. 10/766,503.
Office Action dated Feb. 8, 2008 cited in U.S. Appl. No. 10/766,503.
Office Action dated Jun. 25, 2008 cited in U.S. Appl. No. 10/766,503.

(Continued)

*Primary Examiner* — Irene Marx
*Assistant Examiner* — Satyendra Singh
(74) *Attorney, Agent, or Firm* — Workman Nydegger

(57) ABSTRACT

A method for manufacturing a delivery system that includes a bone growth promoting material encapsulated within a water-absorbing, water-gelatinizable covering used to promote bone growth in order to repair a bone defect and/or strengthen a weakened bone region. The delivery system may be shaped and sized in order to fit within a bleeding wound (e.g., one that is formed in the gingiva when a tooth is extracted). The covering may be formed of a gelatinizable-gauze (e.g., oxidized cellulose) that forms a gel-like material when moistened with water. The delivery system may be stored in a moisture resistant package prior to use.

20 Claims, 4 Drawing Sheets

OTHER PUBLICATIONS

Office Action dated Nov. 18, 2008 cited in U.S. Appl. No. 10/766,503.
Office Action dated Apr. 15, 2009 cited in U.S. Appl. No. 11/549,540.
Office Action dated Nov. 12, 2009 cited in U.S. Appl. No. 11/549,540.
U.S. Appl. No. 11/549,540, filed Jun. 7, 2012, Notice of Allowance.
ASPIDESUTURES.COM—Chromic Catgut, pp. 1-2; accessed on Sep. 10, 2011 on the web: http//www.aspidesutures.com/en/product/absorbable-suture-chromic-catgut.
The term "Substantial" definition from online dictionary at the web—http://www.merriam-webster.com/dictionary/substantial; pp. 1-3.; accessed on Sep. 12, 2011.
U.S. Appl. No. 11/549,540, Sep. 19, 2011, Office Action.
U.S. Appl. No. 11/549,540, Feb. 29, 2012, Office Action.

METHODS OF MANUFACTURING A DELIVERY SYSTEM FOR PROMOTING BONE GROWTH

CROSS REFERENCE TO RELATED APPLICATION

This application is a division of copending U.S. patent application Ser. No. 10/766,503, filed Jan. 28, 2004, now issued U.S. Pat. No. 7,534,264, the disclosure of which is incorporated herein in its entirety.

BACKGROUND OF THE INVENTION

1. Field of the Invention

The present invention relates to the manufacture of delivery systems for promoting and supporting bone growth.

2. Relevant Technology

In dental work, it is often necessary to remove a tooth. Because the teeth are anchored to the jaw bone, removal of the tooth leaves a huge discontinuity or defect in the bone once occupied by the tooth root. In some cases, certain tooth extractions may require the removal of surrounding bone tissue. Whereas the body is, in theory, capable of growing new bone to fill in the discontinuity or defect, bone typically grows very slowly. In fact, bone grows much more slowly than soft tissue, which preferentially grows and fills in much of the void, leaving a weakened, defective bone that is more prone to fracture or failure, particularly in the elderly. Secondarily, once a tooth has been removed, the surrounding jaw bone can atrophy and weaken as a result of non-use in the area of the removed tooth.

In order to restore or augment areas where bone has been removed, naturally derived and synthetically manufactured bone mineral substitutes have been developed. These materials are often used to preserve or augment the alveolar portion of the jaw bone that supports the teeth, augment atrophic alveolar ridges (e.g., tooth socket bones which have decreased in size as a result of tooth removal), and to fill various periodontal defects. Under one current practice, bone mineral substitutes for promoting bone growth in the form of granules are manually delivered into the intended site using a spatula, spoon or other tool. In some cases, these granules are pre-mixed with blood to cause them to adhere together. This method often results in inadvertent spillage and placement of particles into unintended locations and in a general inability to form the material to fill the augmentation site as intended. This is especially the case when attempting to augment bone growth along a ridge, such as the alveolar ridge mentioned above.

In view of the foregoing, it would be an improvement in the art to provide improved delivery systems and related compositions and methods to overcome the aforementioned difficulties.

BRIEF SUMMARY OF THE PREFERRED EMBODIMENTS

The present invention relates to delivery systems and related compositions and methods that may be used to place materials that promote and support bone growth into a bone defect in order to preferentially promote bone growth over the growth of soft tissue. According to one embodiment, the delivery system includes a covering formed of a water-absorbing gelatinizable material, and a bone growth promoting material contained within the covering.

The covering may be formed of any water absorbing gelatinizable material. Suitable materials include, but are not limited to, gelatinizable gauze, oxidized cellulose, oxidized regenerated cellulose, cat gut, or any other hydrophilic absorbable polymer which may be woven, knitted, braided, or otherwise formed into a covering. The material of the covering may be resorbable or non-resorbable by the body, as desired.

Examples of bone growth promoting materials that may be used within the scope of the invention to promote and support the growth of bone into a defect include calcium hydroxyapatite, beta-tricalcium phosphate, purified coral shell, freeze dried natural bone powder, freeze dried natural bone particles, demineralized natural bone powder, and demineralized natural bone particles, shards or fragments. Such materials physically occupy the bone defect so as to (1) physically exclude or displace faster-growing soft tissue that might otherwise fill in an untreated void and (2) form a matrix into which bone can grow over time until the bone growth promoting material is absorbed into the bone and/or integrated into the new bone matrix.

The delivery system may be configured so as to have any desired size and shape. According to one embodiment, the delivery system can have an elongate sausage-like configuration. According to another embodiment, the delivery system can have a pillow-like configuration. The delivery systems according to the invention may be configured so as to fit within whatever size or shape bone effect is being treated.

In an alternative embodiment according to the invention, the bone growth promoting material is enclosed within a syringe, such as in the form of pellets, a powder or mixture of the two. According to one embodiment, the bone growth promoting material is mixed with a tissue adhesion agent, an example of which is the water-absorbing gelatinizable material discussed above, used to form a covering. A gelatinizable gauze or fiber can be chopped, cut-up, or ground into smaller pieces and mixed with the bone growth promoting material. Water or other appropriate solvent or vehicle is mixed with the bone growth promoting material and optional tissue adhesion agent in order to form a paste or gel that can be expressed onto a bone or into a bone defect by means of a syringe. In one embodiment, the water or other solvent or vehicle is added to the syringe and mixed with the bone growth promoting material just prior to use in order to prevent growth of bacteria. Alternatively, an anti-spoilage agent, such as benzalkonium chloride, methylparaben, ethylparaben, and the like, can be added to a pre-mixed composition suitable for long-term storage and subsequent delivery.

The present invention also includes related methods of delivering a bone growth promoting material into a bone defect. In the case of the delivery system comprising bone growth promoting material surrounded by a covering, the delivery device is placed into the bone defect using, e.g., tweezers or other suitable placement device. The covering, being formed of a water-absorbing gelatinizable material, advantageously forms a sticky material that is highly adhesive to bone or other tissue found within the bone defect. In this way, the delivery system is held in place in order to keep the bone growth promoting material within the bone defect. In an alternative method, a bone growth promoting material in the form of a paste or gel is expressed into a bone defect by means of a syringe, preferably in combination with a tissue adhesion agent that helps keep the bone growth promoting material in the desired location.

In order to further protect the bone growth promoting material from foreign debris and/or in order to help maintain the bone growth promoting material within the bone defect being repaired, it is within the scope of the invention to place a barrier layer over the bone growth promoting material. This may be accomplished, for example, by applying a polymerizable resin barrier layer by means of a syringe and then causing or allowing it to harder or cure (e.g., by light or chemical curing).

One preferred use of the inventive compositions, systems and methods is to preserve or restore the alveolar portion of the jaw bone which supports the teeth. When a tooth is removed, the underlying portion of the jaw bone contains a defect that can otherwise fill with soft tissue instead of bone. In addition, bone can atrophy and weaken as a result of non-use and removal of the tooth. Implanting a delivery system containing a bone growth promoting material fills in and strengthens the jaw bone by repairing the defect.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

A detailed description of the delivery systems, compositions and methods of the invention will now be provided with specific reference to Figures illustrating preferred embodiments of the invention. It will be appreciated that like structures will be provided with like reference designations.

The delivery system for promoting bone growth according to one embodiment includes a covering formed of a water-absorbing gelatinizable material and a bone growth promoting and supporting material contained inside, or at least partially surrounding, the covering.

Figure 1A:
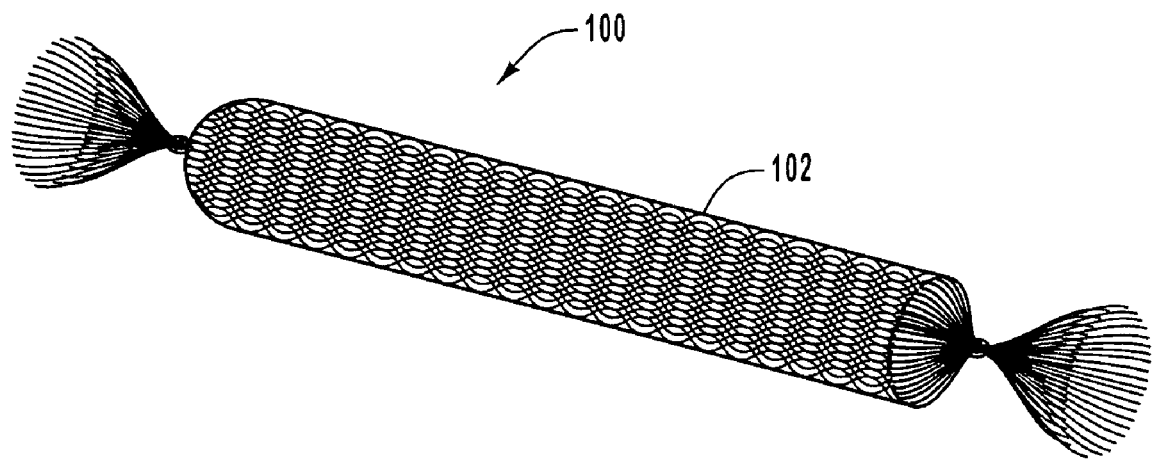
FIG. 1A is a perspective view of an embodiment of a delivery system according to the invention having a sausage-like configuration.

FIG. 1A is a perspective view illustrating one embodiment of a delivery system for promoting bone growth having a covering around at least a portion of a bone growth promoting material. Delivery system 100 includes a covering 102 that encapsulates a bone growth promoting material. In one embodiment, the covering 102 is formed of a water absorbing gelatinizable material, for example, gelatinizable gauze, oxidized cellulose, oxidized regenerated cellulose, cat gut, or any other hydrophilic absorbable polymer which may be woven, knitted, braided, or otherwise formed into a sheet, pouch, tube or other covering. The material of the covering may be resorbable or non-resorbable by the body, as desired. In one embodiment, it advantageously becomes sticky and adhesive toward bone or other tissue where the delivery system 100 is placed.

The bone growth promoting material may be any material that can be used to promote and/or support the growth of bone tissue. Suitable materials may include at least one of calcium hydroxyapatite, beta-tricalcium phosphate, purified coral shell, freeze dried natural bone powder, freeze dried natural bone particles, demineralized natural bone powder, and demineralized natural bone particles, shards or fragments.

Figure 1B:
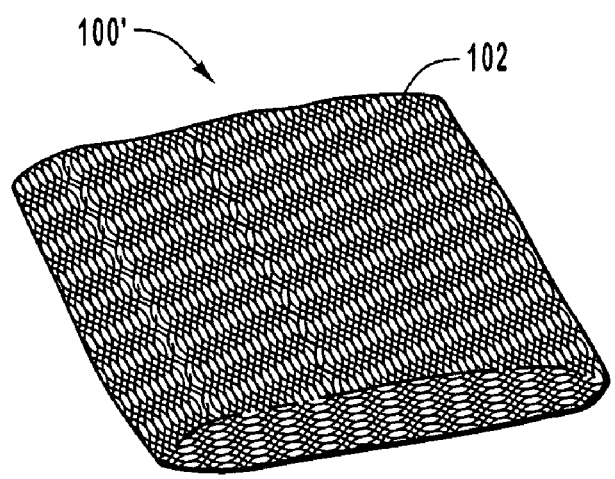
FIG. 1B is a perspective view of an embodiment of a delivery system according to the invention having a pillow-like configuration.

The covering 102 of the delivery system 100 may be woven, knitted or braided to be of any desired shape, size, length, or diameter. Methods of manufacturing the delivery system 100 will be explained in further detail below. According to the embodiment illustrated in FIG. 1A, the delivery system 100 may have an elongated sausage like configuration. FIG. 1B illustrates an alternative embodiment of a delivery system 100' having a pillow like configuration.

According to one embodiment, the delivery system 100 or 100' may also include an adhesive, for example, fibrin powder or chopped adhesive gauze, dispersed within the bone growth promoting material inside covering 102. Including an adhesive may be desirable when the delivery system 100 or 100' is used to promote and support bone growth along a ridge (e.g., an alveolar ridge). The adhesive helps to hold the material together so that the material is not easily displaced from the bone defect into unintended locations once the covering 102 has sufficiently weakened.

The covering 102 as illustrated in FIGS. 1A-1B is formed of a water absorbing gelatinizable material. Suitable materials include gelatinizable thread, oxidized cellulose thread, and oxidized regenerated cellulose thread. These thread materials can be woven, knitted or braided into gauze, which can be used to form a covering 102 having a desired configuration. When the covering 102 is formed of oxidized cellulose thread or oxidized regenerated cellulose thread, the oxidation or oxidation/regeneration necessary to treat the cellulose thread may occur prior to or subsequent to weaving, knitting or braiding. In other words, the covering 102 may be woven, knitted or braided from cellulose thread when initially stronger, and then later chemically treated as desired.

Figure 2:
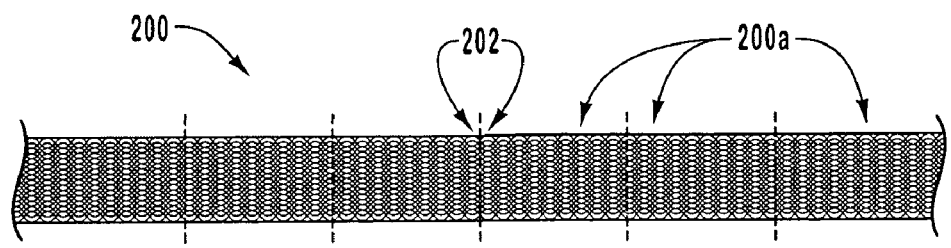
FIG. 2 is a perspective view of a hollow tube prior to sectioning to form individual delivery systems as illustrated in FIGS. 1A and 1B.

For example, the covering 102 of the delivery system 100 of FIG. 1A or delivery system 100' of FIG. 1B may be manufactured by forming a hollow tube 200, as illustrated in FIG. 2. The hollow tube 200 may be long enough to form a plurality of delivery systems 100 or 100'. Hollow tube 200 may be cut into several portions 200a, each portion to be made into a delivery system 100 or. The hollow tube portions 200a may then each be filled with bone growth promoting material, and the ends 202 of each tube portion 200a may then be sealed. The ends 202 may be sealed by tying with a thread, or the ends may be wet sealed. To wet seal the ends 202, each end 202 is closed, wetted with water, and then dried. The water is absorbed by the ends 202 of the covering, which gelatinizes and seals the end 202. Once dried, the result is a delivery system 100 as illustrated in FIG. 1A or delivery system 100' as illustrated in FIG. 1B.

The delivery system 100 or 100' is preferably stored within a moisture resistant package. Examples of such packaging include a foil pouch, a glass or plastic vial, a plastic container, or any other container formed of water resistant material.

The delivery system may be used to promote bone growth in a variety of circumstances. One preferred use is to preserve the alveolar portion of the jaw bone which supports the teeth. When a tooth is removed, the underlying portion of the jaw bone will contain a defect that can greatly weaken the bone. In addition, the bone may atrophy and weaken as a result of non-use and removal of the tooth. Implanting a delivery system containing a bone growth promoting material displaces soft tissue growth in favor of bone growth so as to strengthen the area of the jaw bone into which it is implanted.

Figure 3:
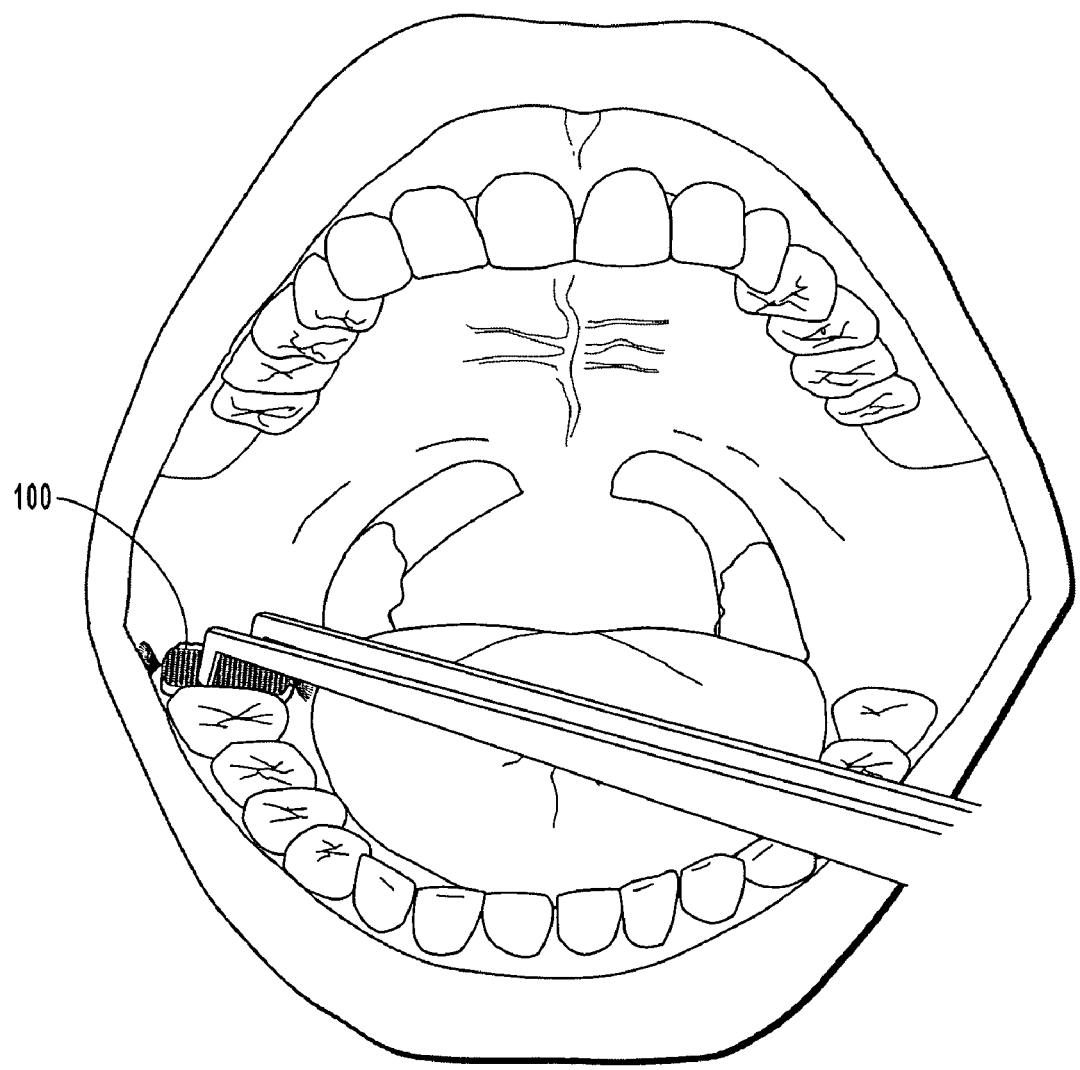
FIG. 3 is a perspective view of a tooth extraction site where a delivery system similar to the one illustrated in FIG. 1A is being placed.

FIG. 3 is a perspective view of a portion of a patient's mouth where the third molar has just been removed. A delivery system 100 is shown being placed into the void or defect left as a result of removal of the tooth from the jaw bone. The delivery system 100 is placed adjacent to the jaw bone tissue so as to selectively promote growth of the bone tissue and prevent the incursion of faster-growing soft tissue. As mentioned above, the covering 102 of the delivery system 100 may be resorbable or non-resorbable, as desired. It may also be adhesive in order to help maintain the delivery system 100 in place.

Either delivery system 100 or 100' can be used to promote bone growth along a ridge (e.g., alveolar ridge) or any other place where a bone defect or weakened bone exists. Other delivery systems of alternative shape and design could also be used as desired. When placed along a ridge, it may be desirable to include an adhesive dispersed within the material. The adhesive helps to hold and maintain the bone growth promoting material together so that it does not slide down the side of the ridge as the covering 102 weakens over time.

Figure 4A:
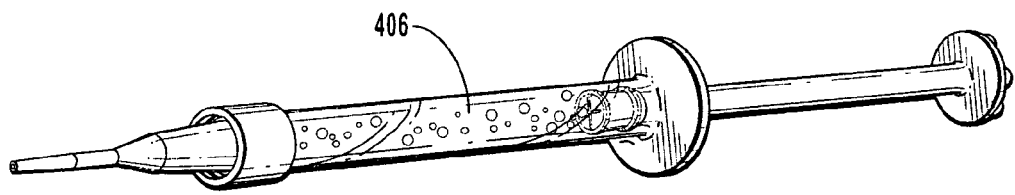
FIGS. 4A and 4B illustrate use of a syringe delivered bone growth promoting composition.
Figure 4B:
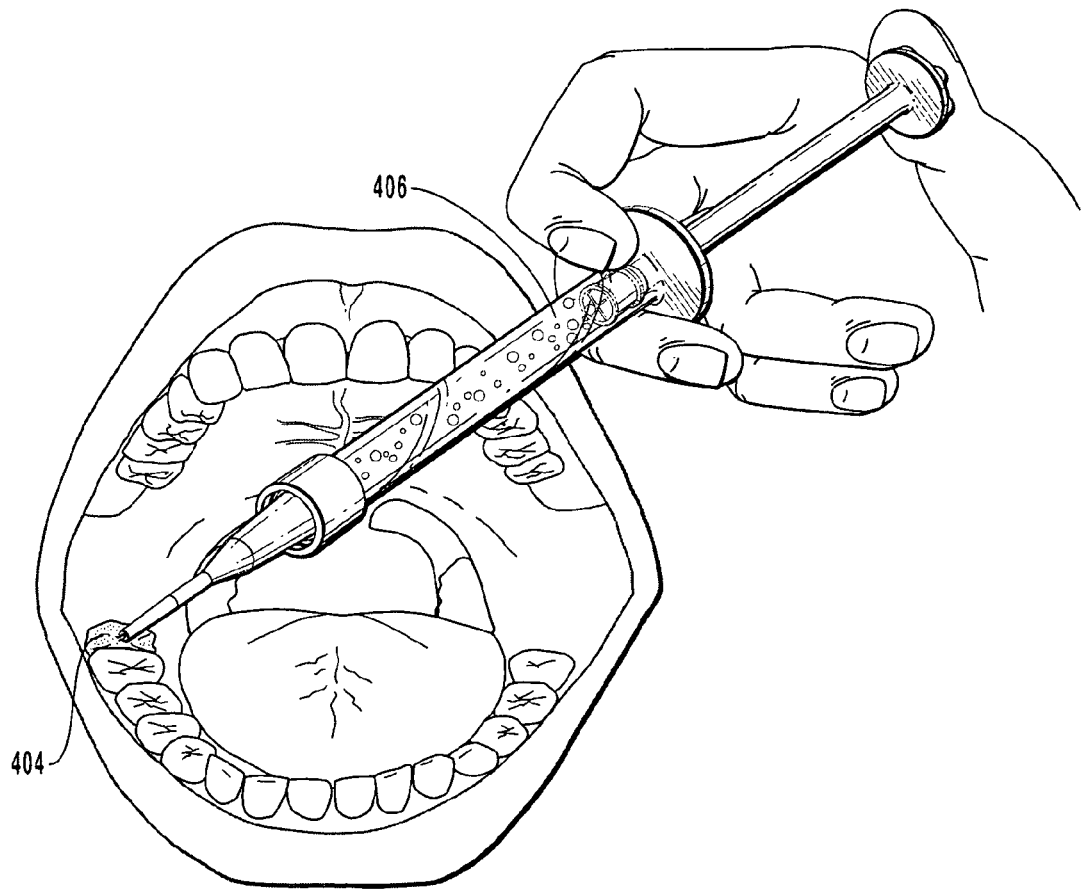

According to another embodiment within the scope of the invention, a syringe delivered bone growth promoting composition 404 may be dispensed from a syringe 406, as illustrated in FIGS. 4A and 4B. The composition 404 may comprise a bone growth promoting material in granule or powder form, and a thickener dispersed among the bone growth promoting material. The thickener may also be adhesive to tissue and may comprise any of gelatinizable gauze, oxidized cellulose, oxidized regenerated cellulose, or cat gut either ground up or in powder form. The thickener may alternatively comprise any proteinous material, for example, a biocompatible gelatinous collagen. The thickener is advantageously dispersed among the bone growth promoting material.

Upon the addition of water or other solvent or vehicle, the composition 404 is capable of forming a viscous gel or firm putty (depending on the amount of water added) that may be dispensed from the syringe 406. The composition 404 may initially be provided in either a dry or wet form. In other words, water may be added at the time of manufacture or later, by the dental practitioner. If provided in a wet form, a preservative (e.g., benzalkonium chloride, methylparaben, ethylparaben, and the like) capable of preventing growth of bacteria or other microorganisms is preferably included. The viscous gel or firm putty may be dispensed in the location desired, as illustrated in FIG. 4B, and in the case of a firm putty, may be formed as desired by the dental practitioner.

Figure 5:
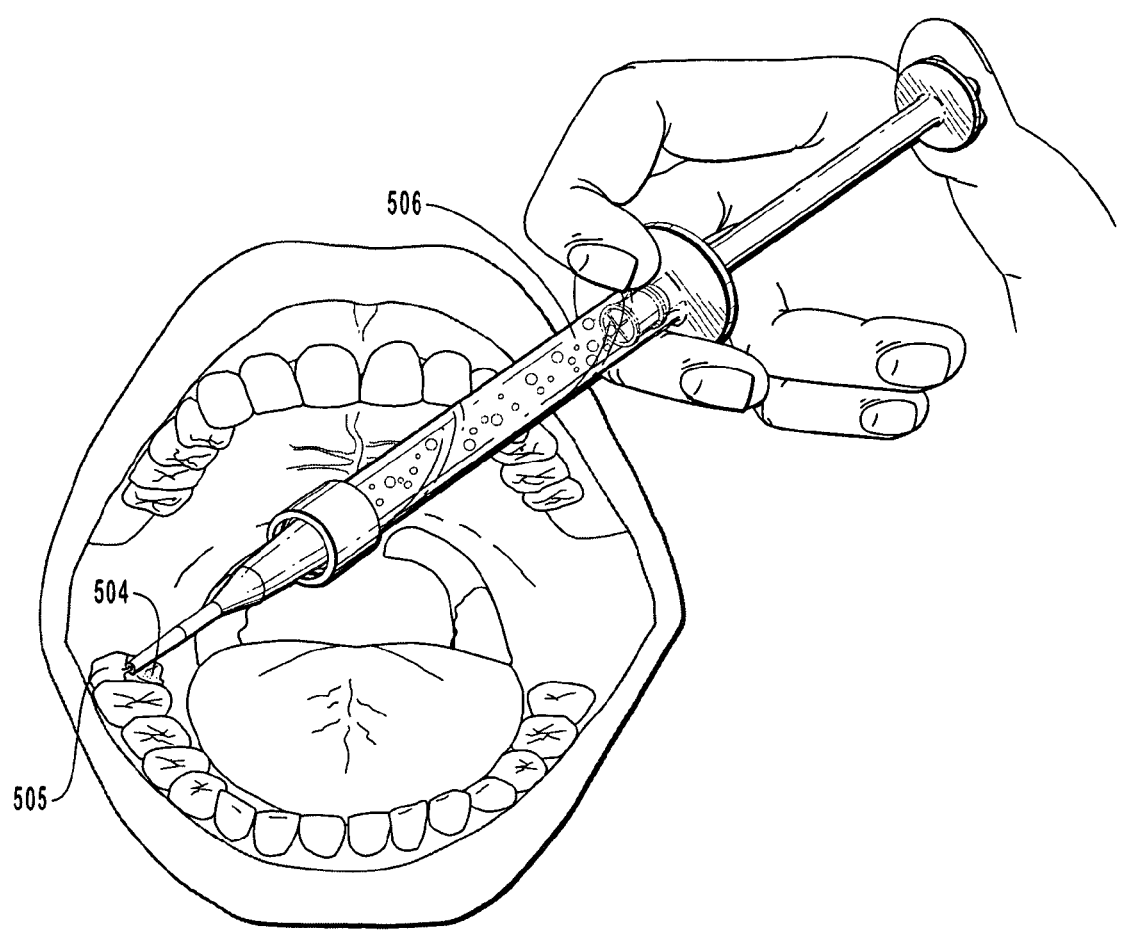
FIG. 5 illustrates an alternative method of augmenting bone growth with a bone growth promoting material and a syringe delivered polymerizable resin barrier layer.

FIG. 5 illustrates a further alternative embodiment. In this embodiment, a polymerizable resin 505 is delivered by a syringe 506 over bone growth promoting material 504 that has been packed adjacent to bone tissue to be augmented. The polymerizable resin preferably is a resorbable, biocompatible material that may be light or chemically cured. It acts as a barrier layer to prevent saliva or other fluids from carrying away the packed bone growth promoting material. It also reduces migration of fast-growing epithelial tissue down into the implanted material, thus facilitating bone growth in from the side. The bone is thereby allowed to grow into the packed bone growth promoting material free of completion from epithelial tissue.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing a delivery system for promoting bone growth comprising:
   forming a water-absorbing, water-gelatinizable material that becomes gelatinous and self-adhesive when moistened with water into a hollow tube or pouch having an initially open end;
   inserting a bone growth promoting material into the hollow tube or pouch through the initially open end;
   closing the initially open end of the tube or pouch;
   moistening the closed end with water so that it temporarily becomes gelatinous and self-adhesive; and
   drying the closed, moistened, and self-adhesive end to form a sealed end of the tube or pouch and thereby form a delivery system for promoting bone growth comprised of:
      an outer covering formed from the water-absorbing, water-gelatinizable material that defines an interior space; and
      the bone growth promoting material encapsulated within the interior space by the outer covering,
      wherein the outer covering becomes sticky and adhesive to tissue in a bone void when moistened with water.

2. A method as recited in claim 1, the hollow tube or pouch including a plurality of initially open ends that are closed, moistened with water, and dried to form a plurality of sealed ends.

3. A method as recited in claim 1, wherein drying causes the gelatinous and self-adhesive material to harden so as to form a dried seal.

4. A method as recited in claim 1, further comprising:
   dividing the tube or pouch into individual sections,
   individually wet sealing ends of each individual section so as to form a plurality of delivery systems from a single tube or pouch filled with the bone growth promoting material, and
   separating the delivery systems prior to use.

5. A method as recited in claim 1, wherein the water-absorbing, water-gelatinizable material is formed in an intermediate process by oxidizing an intermediate covering material that is initially non-water-absorbing and non-water-gelatinizable prior to being oxidized.

6. A method as recited in claim 5, wherein the covering material is oxidized in the intermediate process prior to inserting the bone growth promoting material into at least a portion of the tube or pouch.

7. A method as recited in claim 5, wherein the covering material is oxidized in the intermediate process after inserting the bone growth promoting material into at least a portion of the tube or pouch.

8. A method as recited in claim 1, wherein the water-absorbing, water-gelatinizable material comprises oxidized cellulose, gelatinizable gauze, oxidized regenerated cellulose, or gelatinizable cat gut.

9. A method as recited in claim 1, wherein the bone growth promoting material comprises at least one of calcium hydroxyapatite, beta-tricalcium phosphate, purified coral shell, freeze dried natural bone powder, freeze dried natural bone particles, demineralized natural bone powder, or demineralized natural bone particles, shards or fragments.

10. A method as recited in claim 1, wherein the delivery system has an elongate sausage-like configuration comprising at least one wet sealed end.

11. A method as recited in claim 1, wherein the delivery system has a pillow-like configuration comprising at least one wet sealed end.

12. A method as recited in claim 1, further comprising placing the delivery system into a moisture-resistant package in order to maintain the outer covering in a dry condition prior to use and prevent premature gelatinization prior to placement into the bone void.

13. A method as recited in claim 1, further comprising dispersing an adhesive within the bone growth promoting material.

14. A method as recited in claim 13, wherein the adhesive comprises at least one of fibrin powder or chopped adhesive gauze.

15. A method of manufacturing a delivery system for promoting bone growth comprising:
   forming a non water-gelatinizable cellulose fabric into a hollow tube or pouch;
   inserting a bone growth promoting material into the tube or pouch;
   after inserting the bone growth promoting material into the tube or pouch, oxidizing the cellulose fabric in order to convert it into a water-absorbing, water-gelatinizable material that becomes sticky and adhesive to tissue in a bone void when moistened with water; and
   closing one or more initially open ends of the tube or pouch to form a delivery system for promoting bone growth comprised of:
      an outer covering formed from the water-absorbing, water-gelatinizable material that defines an interior space, and
      the bone growth promoting material encapsulated within the interior space by the outer covering,
      wherein the outer covering becomes sticky and adhesive to tissue in a bone socket when moistened with water.

16. A method as recited in claim 15, wherein closing one or more initially open ends of the tube or pouch comprises wet sealing and drying the ends.

17. A method as recited in claim 15, further comprising:
   dividing the tube or pouch into individual sections, and
   individually wet sealing and drying ends of each individual section so as to form a plurality of delivery systems from a single tube or pouch filled with the bone growth promoting material.

18. A method of manufacturing a delivery system for promoting bone growth comprising:
   forming an oxidized cellulose gauze into a hollow tube or pouch having an initially open end, the oxidized cellulose gauze becoming gelatinous and self-adhesive when moistened with water;
   inserting a bone growth promoting material the hollow tube or pouch through the initially open end;
   closing and applying moisture to the initially closed end so that it temporarily becomes gelatinous and self-adhesive; and
   drying the closed and moistened end to form a sealed end of the tube or pouch and thereby form a delivery system for promoting bone growth comprised of:
      an outer covering formed from the water-absorbing, water-gelatinizable material that defines an interior space; and
      the bone growth promoting material encapsulated within the interior space by the outer covering,
      wherein the outer covering becomes sticky and adhesive to tissue in a bone socket when moistened with water.

19. A method as recited in claim 18, further comprising:
   dividing the tube or pouch into individual sections; and
   then individually wet sealing and drying ends of each individual section so as to
   form a plurality of delivery systems from a single tube or pouch filled with the bone growth promoting material,
   wherein the plurality of delivery systems can be separated into individual delivery systems prior to use.

20. A method as recited in claim 18, wherein the bone growth promoting material comprises at least one of calcium hydroxyapatite, beta-tricalcium phosphate, purified coral shell, freeze dried natural bone powder, freeze dried natural bone particles, demineralized natural bone powder, or demineralized natural bone particles, shards or fragments.

* * * * *

UNITED STATES PATENT AND TRADEMARK OFFICE
CERTIFICATE OF CORRECTION

| | |
|---|---|
| PATENT NO. | : 8,323,339 B2 |
| APPLICATION NO. | : 12/202886 |
| DATED | : December 4, 2012 |
| INVENTOR(S) | : Fischer |

Page 1 of 1

It is certified that error appears in the above-identified patent and that said Letters Patent is hereby corrected as shown below:

In the Specification

Column 3
Line 5, change "harder" to --harden--

Column 4
Line 56, change "100 or. The" to --100, or the--

In the Claims

Column 7
Line 8, change "elongate" to --elongated--
Line 17, change "the" to --a--

Column 8
Line 16, change "material the" to --material into the--

Signed and Sealed this
Sixth Day of August, 2013

Teresa Stanek Rea
*Acting Director of the United States Patent and Trademark Office*